(12) United States Patent
Schumaier et al.

(10) Patent No.: US 8,870,558 B2
(45) Date of Patent: Oct. 28, 2014

(54) EARPLUG SHAPER HAVING CURVED SHAPING SURFACES

(75) Inventors: Daniel R. Schumaier, Elizabethton, TN (US); David M. Campbell, II, Johnson City, TN (US); Jerry V. Foster, Lawrenceville, GA (US); Harry S. Strothers, IV, Chamblee, GA (US); Allison Guyton, Lawrenceville, GA (US); Jason R. Herman, Lawrenceville, GA (US); Christopher S. Kudika, Duluth, GA (US); Scott A. Lutz, Atlanta, GA (US); Stephen J. Drabant, Lawrenceville, GA (US); Katherine A. King, Gainesville, GA (US)

(73) Assignee: Daniel R. Schumaier, Elizabethton, TN (US)

( * ) Notice: Subject to any disclaimer, the term of this patent is extended or adjusted under 35 U.S.C. 154(b) by 454 days.

(21) Appl. No.: 13/177,105

(22) Filed: Jul. 6, 2011

(65) Prior Publication Data
US 2013/0011509 A1    Jan. 10, 2013

(51) Int. Cl.
*B28B 11/10* (2006.01)
*A61F 11/08* (2006.01)
*B29C 44/34* (2006.01)

(52) U.S. Cl.
CPC ............ *B29C 44/3496* (2013.01); *A61F 11/08* (2013.01)
USPC ................ 425/2; 425/233; 425/318; 425/333; 425/337; 425/395; 425/402; 425/409; 425/458

(58) Field of Classification Search
USPC ......... 425/2, 12, 87, 318, 458, 408, 409, 410, 425/411, 233, 332, 333, 335, 337, 362, 374, 425/391, 394, 395, 402
See application file for complete search history.

(56) References Cited

U.S. PATENT DOCUMENTS

| | | | |
|---|---|---|---|
| 4,753,412 A * | 6/1988 | Johnson | 249/55 |
| 5,006,055 A * | 4/1991 | Lebisch et al. | 425/2 |
| 5,195,539 A | 3/1993 | Dyrud et al. | |
| 5,322,185 A | 6/1994 | Leight | |
| 5,609,164 A | 3/1997 | Dyrud et al. | |
| 5,988,313 A * | 11/1999 | Håkansson | 181/135 |
| 6,283,339 B1 * | 9/2001 | Morrow | 222/452 |
| 6,440,339 B1 * | 8/2002 | Magidson et al. | 264/46.4 |
| 7,192,544 B2 * | 3/2007 | Jenkins et al. | 264/46.4 |
| 7,220,372 B2 * | 5/2007 | Woo et al. | 264/46.7 |
| 7,232,304 B2 * | 6/2007 | Killion | 425/318 |
| 7,247,011 B2 * | 7/2007 | St. Germain et al. | 425/87 |
| 7,614,867 B2 | 11/2009 | Schumaier | |
| 7,727,433 B2 * | 6/2010 | Knauer et al. | 264/46.4 |

(Continued)

*Primary Examiner* — Seyed Masoud Malekzadeh
(74) *Attorney, Agent, or Firm* — Luedeka Neely Group, P.C.

(57) ABSTRACT

An earplug shaping device compresses a compressible earplug prior to insertion of the earplug into a user's ear canal. The device includes a first member and a second member which rotate with respect to each other. The outer surface of the first member and inner surface of the second member define a space that decreases in size as the first and second members rotate with respect to each other, thereby compressing the compressible earplug. Various embodiments of the earplug shaper employ a ratchet mechanism permitting substantially only one direction of rotation.

13 Claims, 5 Drawing Sheets

(56) References Cited

U.S. PATENT DOCUMENTS

| | | | |
|---|---|---|---|
| 7,731,487 B2 * | 6/2010 | Knauer et al. | 425/4 R |
| 7,998,391 B1 * | 8/2011 | Koo | 264/255 |
| 8,061,472 B2 * | 11/2011 | Tiemens | 181/135 |
| 8,343,397 B2 * | 1/2013 | Woo et al. | 264/46.4 |
| 2006/0138691 A1 * | 6/2006 | Knauer et al. | 264/46.4 |
| 2007/0227546 A1 | 10/2007 | Schumaier | |
| 2008/0116219 A1 | 5/2008 | Lawrence | |
| 2009/0304981 A1 * | 12/2009 | Wu | 428/81 |

* cited by examiner

EARPLUG SHAPER HAVING CURVED SHAPING SURFACES

FIELD

This invention relates generally to earplug shaping devices. More particularly, the present invention relates to a portable device uniquely configured to uniformly shape PVC, polyethylene and other resilient/slow recovery earplugs to a proper pre-insertion diameter to enhance effective use of the earplugs.

BACKGROUND

In manufacturing, construction and other noisy environments, continued exposure to high sound levels can cause hearing loss. Repeated exposure to noise levels above 90 decibels can cause hearing loss in a relatively short time. Hearing loss has become such a problem in the United States that OSHA requires any workers who are continually exposed to an ambient noise level above 90 decibels to wear hearing protection.

Hearing loss arising out of continued exposure to high sound levels can easily be avoided or greatly reduced by the use of hearing protection devices, such as earmuffs or earplugs. Earmuffs typically have a cup or shell which fits over the top of the ear with padding in between the shell and the user's head which helps seal out noise. While earmuffs generally work well, they are typically awkward to wear, uncomfortable and can interfere with the wearer's activities.

Resilient earplugs (also known as "slow recovery" earplugs) provide an alternative means of hearing protection against the noise an individual is subjected to. Resilient earplugs can be fabricated from a variety of materials including silicon, various plastics, PVC and polyethylene. Two of the more common materials used are PVC and polyethylene. These materials provide an earplug which can be compressed to a small diameter and inserted into the ear canal. Once in the ear canal, the earplug slowly expands or recovers to seal against the interior surface of the ear canal, thereby inhibiting noise or sound from entering the ear canal.

Pre-insertion shaping of the earplug is typically accomplished by rolling the earplug between the thumb and index finger. Unfortunately, users frequently fail to roll and compress the earplugs to the proper pre-insertion diameter. When this happens, the earplug will not function to its full potential.

Another problem associated with resilient earplugs occurs when creases are introduced into the outer surface of the earplug as it is being rolled and compressed. Creases introduced during pre-insertion shaping of the earplug can provide a pathway for sound to enter the ear canal, which further reduces the effectiveness of the earplug.

Yet another problem associated with resilient earplugs is that dirt and grime is often transferred from the user's hands to the earplug as it is being handled and shaped prior to insertion. In addition to being unsightly, soiled earplugs have the potential to introduce infectious pathogens into the ear canal. And because of their unsightly appearance, soiled earplugs are often discarded after only one use, which is wasteful.

While there currently exist devices capable of rolling earplugs, these devices are not portable. Additionally, prior earplug rolling devices are not capable of being easily disassembled for cleaning and also do not provide the capability of storing earplugs within the device.

For the foregoing reasons, there is a need for an earplug shaping device that is portable and enhances the use and effectiveness of resilient earplugs.

SUMMARY

The present invention is directed to a portable device for pre-insertion shaping of a resilient earplug to a proper diameter without introducing creases in the surface of the plug. The device includes first and second members that compress an earplug when the two members are rotated with respect to each other. Either the first or the second member may have a radius that varies from minimum value to a maximum value, while the other member has a substantially constant radius. Various embodiments of the present invention also include a cap configured to enclose the space between the two members, in addition to a hollow container for storing unused earplugs.

Some embodiments are directed to an apparatus having a first member, a second member, and a space there between. The first member, which is configured to rotate about a rotational axis, has an outer surface for contacting the earplug. The outer surface of the first member is disposed about the rotational axis at a distance $R_1$ from the rotational axis. The distance $R_1$ varies from a minimum value at a first location on the outer surface to a maximum value at a second location on the outer surface. The second member has an inner surface for contacting the earplug. The inner surface is disposed about the rotational axis at a substantially constant distance $R_2$ from the rotational axis, where $R_2$ is greater than $R_1$. Between the outer surface of the first member and the inner surface of the second member is the space for accommodating the earplug. When the device is operated, the earplug is compressed between the outer surface of the first member and the inner surface of the second member as the first member rotates about the rotational axis in relation to the second member. Alternatively, the second member may rotate about the rotational axis in relation to the first member.

In some embodiments, the outer surface of the first member is disposed about the rotational axis at a substantially constant distance $R_1$ from the rotational axis, and the inner surface of the second member is disposed about the rotational axis at a distance $R_2$ which is greater than the distance $R_1$, and the distance $R_2$ varies from a minimum value at a first location on the inner surface to a maximum value at a second location on the inner surface.

In some embodiments, the outer surface of the first member is disposed about the rotational axis at a distance $R_1$ which varies from a minimum value at a first location on the outer surface to a maximum value at a second location on the outer surface. In these embodiments, the inner surface of the second member is disposed about the rotational axis at a distance $R_2$ which is greater than the distance $R_1$, and the distance $R_2$ varies from a minimum value at a first location on the inner surface to a maximum value at a second location on the inner surface.

One of the advantages of a curved roller structure over a linear structure is that the distance necessary to get a full compression of an earplug can be accommodated within a fairly compact and portable package. An equivalent length linear path would be too long to practically implement because the product would be too large to be carried with the user. Also, the longer rolling surface of the embodiments described herein allows a wider variety of models of earplugs to be rolled using one rolling device.

Another advantage of some embodiments described herein is the provision of a storage compartment for storing earplugs within the structure.

Yet another advantage is that the design allows for the device to be taken apart and cleaned. Maintaining the cleanliness of the earplugs reduces the amount of dirt and/or bacteria in the ear.

Yet another advantage is in the process of turning the device to move the first member relative to the second member. The turning process generally slows down the process of rolling which makes for a more consistent compression, whereas prior shaping devices having linear shaping surfaces required one linear move which could occur too rapidly, causing improper compression.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

DETAILED DESCRIPTION

Figure 1:
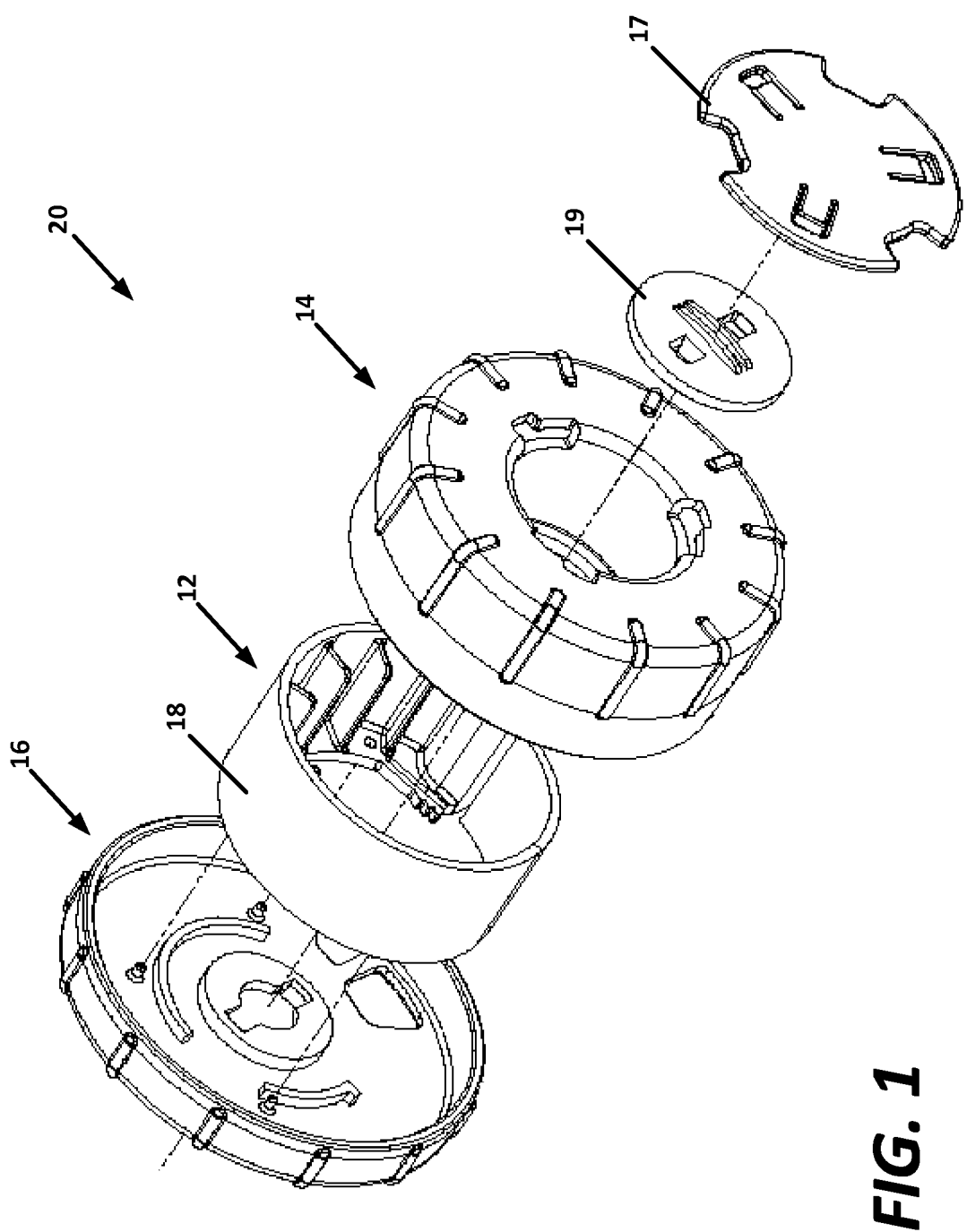
FIG. 1 shows an exploded view of an embodiment of an earplug shaper.

Preferred embodiments of the present invention will now be described with reference to the accompanying drawings, wherein like reference characters designate like or similar parts throughout. The terminology used herein is intended to be interpreted in its broadest reasonable manner, even though it is being utilized in conjunction with a detailed description of certain specific preferred embodiments of the present invention. This is further emphasized below with respect to some particular terms used herein. Any terminology intended to be interpreted by the reader in any restricted manner will be overtly and specifically defined as such in this specification.

With respect to the embodiment of FIG. 1, a resilient earplug shaper 20 includes a first member 12, a second member 14 and a cap member 16. The first member 12, second member 14 and cap member 16 may be fabricated from a variety of materials including wood, metal, plastic and composite materials. In a preferred embodiment, the first member 12, second member 14 and cap member 16 are molded from polycarbonate.

The first member 12 includes an outer surface 18 configured to rotate about a rotational axis with respect to the second member 14. In a preferred embodiment illustrated in FIG. 2, the radius R1 of the outer surface of the first member 12 is variable, and varies from a minimum value R1' at a first point P1 to a maximum value R1" at a second point P2. Most preferably the radius R1 of the outer surface 18 of the first member varies constantly between the first point P1 and the second point P2 such that the radius R1 of the outer surface 18 of the first member 12 substantially defines a spiral. In an alternative embodiment, the radius R1 of the outer surface 18 of the first member 12 is constant, such that the radius R1 of the outer surface 18 of the first member 18 substantially defines a circle.

Figure 2:
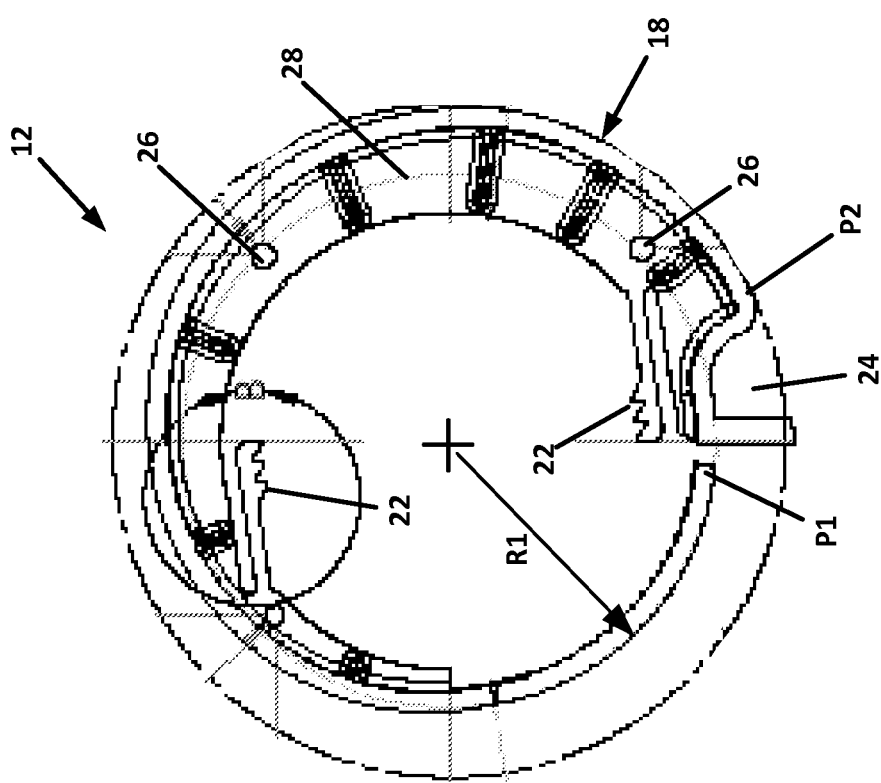
FIG. 2 shows a top view of a first member of the embodiment of FIG. 1.

In the embodiment illustrated in FIG. 2 the first member 12 includes one or more ratchet arms 22. The ratchet arms 22 are preferably connected to an upper lip portion 28 of the first member 12 and are disposed within the radius defined by the outer surface 18. As shown in FIG. 2, the ratchet arms 22 preferably extend inward with respect to the outer surface 18 of the first member 12. With respect to FIG. 3, each ratchet arm 22 includes one or more teeth 32 that are uniformly disposed toward an end of the ratchet arm 22. The teeth 32 of the ratchet arm 22 are generally facing toward the rotational axis of the first member 12.

With further reference to FIG. 2, the first member 12 also preferably includes a cavity 24 at least partially defined by an indentation in the outer surface 18. The cavity 24 is substantially disposed near the second point P2 of the outer surface 18.

The first member 12 also preferably includes one or more apertures 26 positioned around the circumference of the upper lip portion 28 of the first member 12.

Figure 4:
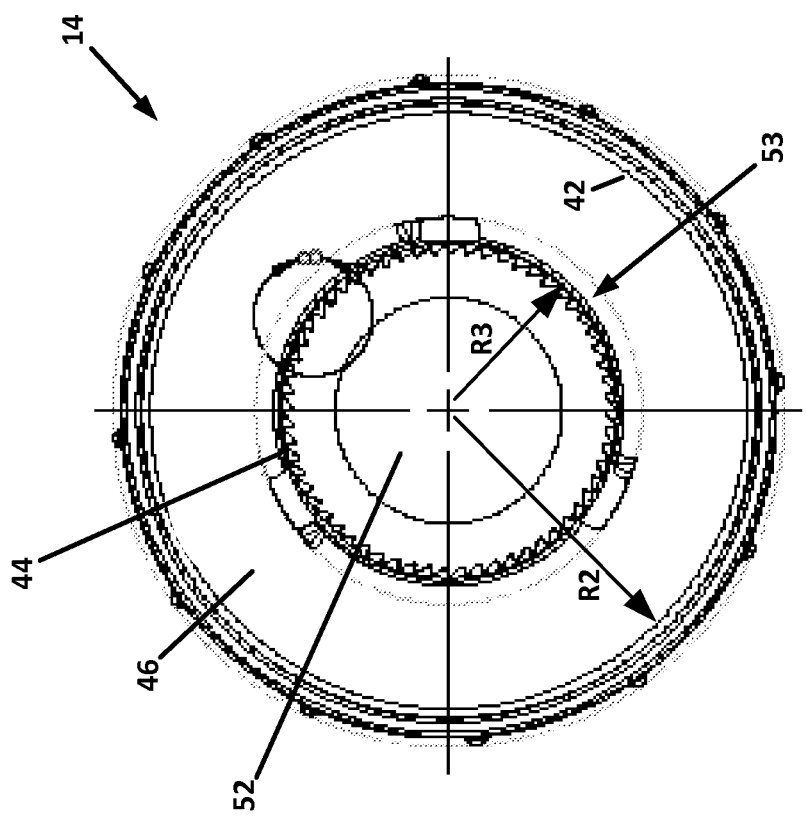
FIG. 4 shows a top view of a second member, a container, and a bottom member of the embodiment of FIG. 1.

FIG. 4 illustrates a preferred embodiment of the second member 14. The second member 14 includes an inner surface 42 that is configured to rotate about the rotational axis with respect to the first member 12. In a preferred embodiment, the radius R2 of the inner surface 42 of the second member 14 is substantially constant so as to define a circle. However, in alternative embodiments, the radius R2 of the inner surface of the second member 14 may vary from a minimum value at a first location to a maximum value at a second location, and in some embodiments the radius R2 of the inner surface 42 of the second member 14 substantially defines a spiral. Additionally, the second member 14 includes a bottom surface 46 that substantially encloses a lower portion of the second member 14.

Figure 5:
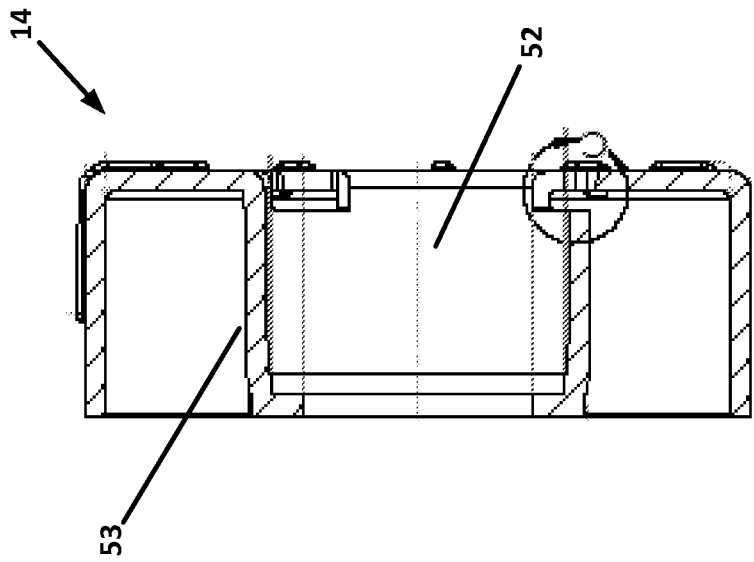
FIG. 5 shows a cross-sectional side view of the second member, container, and bottom member of the embodiment of FIG. 1.

As shown in FIG. 5, the second member 14 may also include a hollow cylindrical storage cavity 52 disposed centrally about the rotational axis. The hollow storage cavity 52 has a radius R3 that is less than the radius R1 of the first member 12.

As shown in FIG. 4, the second member 14 preferably includes a plurality of notches 44 disposed radially about the rotational axis. The notches 44 are preferably formed in an external surface 53 of the hollow storage cavity 52, with the radius of the notches 44 being substantially equivalent to the radius R3 of the hollow storage cavity 52.

Figure 6:
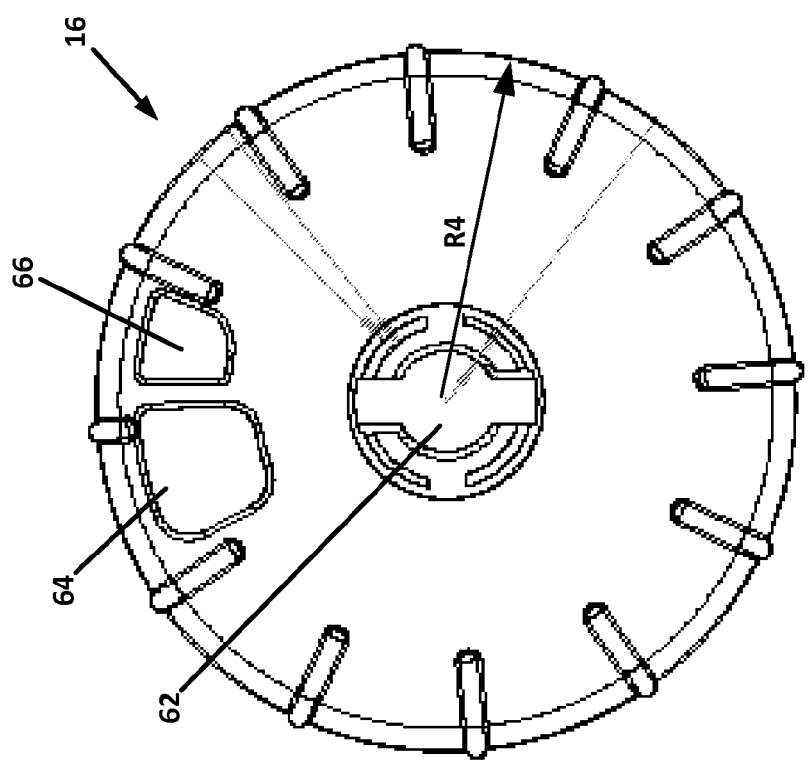
FIG. 6 shows a top view of a cap member of the embodiment of FIG. 1.

FIG. 6 illustrates a cap member 16 according to a preferred embodiment. The cap member 16 preferably defines a circle having a radius R4 that is greater than the radius R2 of the inner surface 42 of the second member 14. The cap member 16 preferably includes a keyhole 62 located at the center of the cap member 16. The cap member 16 preferably includes both a first passageway 64 and a second passageway 66. The first passageway 64 is sized such that a fully uncompressed earplug may pass through the first passageway 64. The second passageway 66 is preferably sized such that a fully compressed earplug may pass through the second passageway 66.

Figure 7:
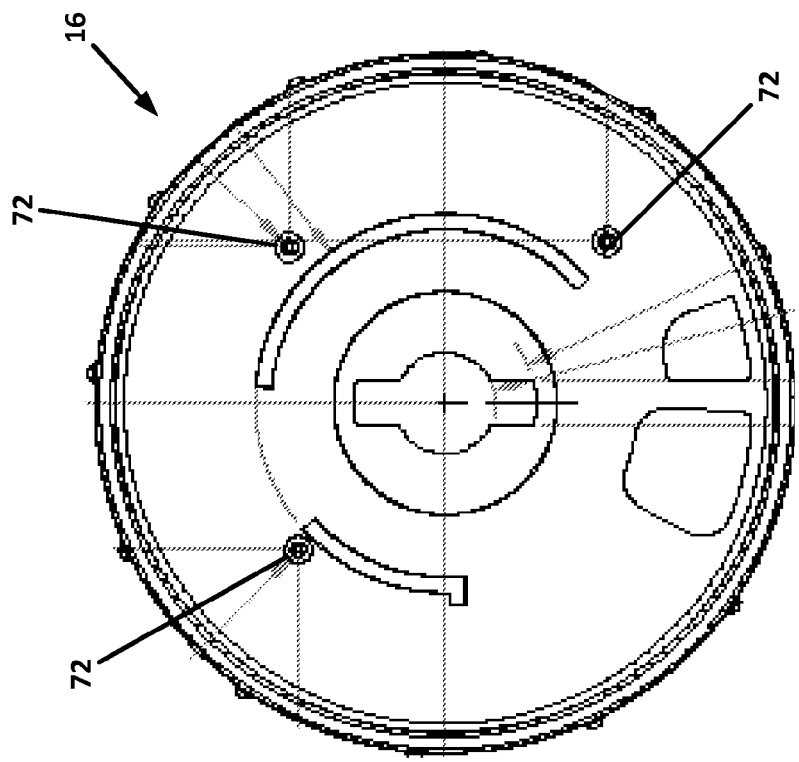
FIG. 7 shows a bottom view of the cap member.

With reference to FIG. 7, the cap member 16 further includes one or more pins 72. The outside diameter of the pins 72 is preferably sized such that the pins 72 may be press fit into the apertures 26 of the first member 12, thereby substantially connecting and securing the cap member 16 to the first member 12.

Figure 8:
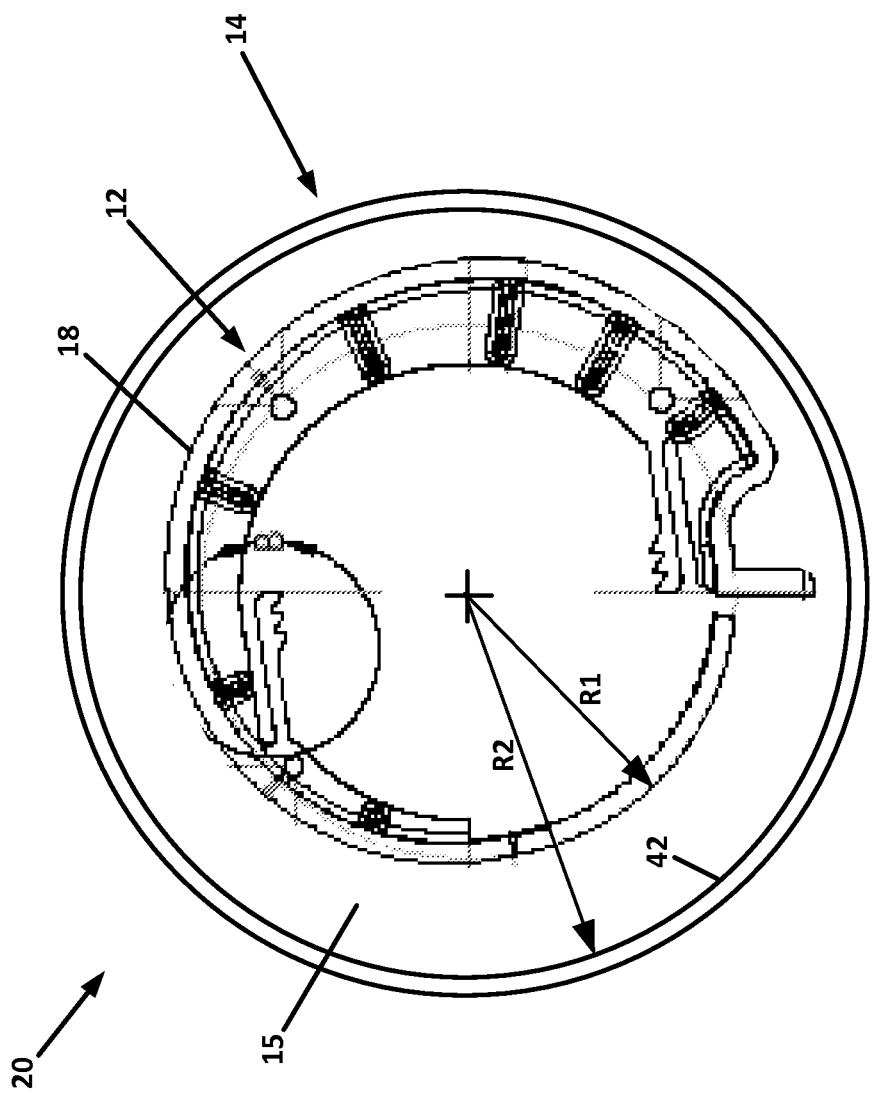
FIG. 8 shows a cross-sectional view of the first member disposed in relation to the second member.

With reference to FIG. 8, the first member 12 is preferably placed within the second member 14 such that the axes of rotation of the two members are substantially collinear. In this position, there is a space 15 defined between the outer surface 18 of the first member 12 and the inner surface 42 of the second member.

The cap member 16 is placed over the second member 14 and engages the first member 12 as the pins 72 of the cap member 16 press into the apertures 26 of the first member 12. A key member 19 is preferably positioned within the hollow storage cavity 52 and engages the keyhole 62, thereby securing the cap member 16 to the second member 14 and capturing the first member 12 between the cap member 16 and the second member 14. A removable cover member 17 may be attached to the outer portion of the second member 14 causing the hollow storage cavity 52 to be substantially enclosed.

In a preferred embodiment, the outer surface 18 of the first member 12 and the inner surface 42 of the second member 14 are textured, such as with dimpling or ridges or other texturing that introduces friction between the surface 18 and the earplug and between the surface 42 and the earplug. It is desirable for the earplug to roll between the surfaces 18 and 42 as it is compressed between them. The texturing on the surfaces 18 and 42 prevents the earplug from slipping with respect to the surfaces and promotes rolling.

To use the earplug shaper 20, a resilient earplug is inserted into the resilient earplug shaper 20 through the first passageway 64 such that it is capture between the outer surface 18 of the first member 12 and the inner surface 42 of the second member 14 at the first point P1. The combination of the cap member 16 and the first member 12 is rotated with respect to the second member 14. In a preferred embodiment, as the cap member 16 and first member 12 rotate with respect to the second member 14, the distance between the outer surface 18 of the first member 12 and the inner surface 42 of the second member 14 decreases at the location where the earplug is captured between the two surfaces. This causes the earplug to be rolled and compressed between the outer surface 18 of the first member 12 and the inner surface 42 of the second member 14 until the earplug reaches the second point P2 of the first member 12. The fully compressed earplug then passes into the cavity 24, which is preferably in alignment with the second passageway 66. The resilient earplug shaper 20 is then preferably turned upside down to eject the fully compressed earplug for insertion into the user's ear.

Figure 3:
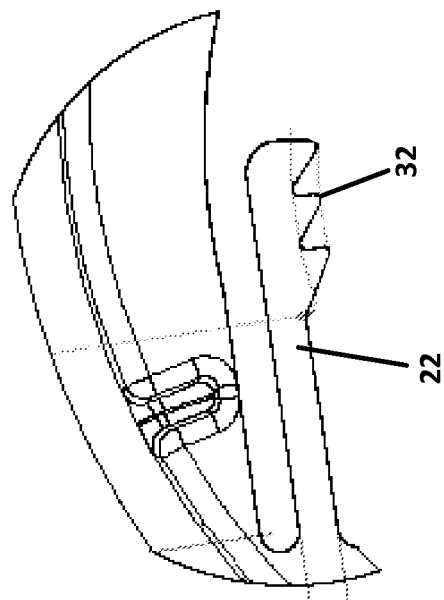
FIG. 3 shows a view of a ratchet arm of the first member depicted in FIG. 2.

With reference to the embodiment depicted in FIGS. 2, 3 and 4, the ratchet arm 22 of the first member 12 engages the notches 44 of the second member 14. When the cap member 16 and the first member 12 rotate together in relation to the second member 14, the teeth 32 of the ratchet arm 22 engage the notches 44 of the second member 14. The notches 44 of the second member 14 are preferably directional in shape, such that as the teeth 32 of the ratchet arm 22 engage the notches 44 of the second member 14, only one direction of rotation is permitted.

In preferred embodiments, the outer surface 18 of the first member 12 has a radius R1 that varies from a first point P1 to a second point P2, so as to define a spiral, and the inner surface 42 of the second member 14 defines a circle. However, in other embodiments the inner surface 42 of the second member 14 has a radius R2 that varies from a minimum value at one point to a maximum value at another point, and the outer surface 18 of the first member 12 substantially defines a circle. In yet other embodiments, the inner surface 42 of the second member 14 and the outer surface 18 of the first member 12 both have a radius that varies from a maximum value to a minimum value. Accordingly, embodiments of the invention include any other like configuration wherein the first member 12 rotates in relation to the second member 14, thereby causing the space 15 at any particular point between the outer surface 18 of the first member 12 and the inner surface 42 of the second member 14 to decrease as the two members are rotated in relation to each other.

In an alternative embodiment of the present invention, an electrical motor is preferably mounted within the resilient earplug shaper 20, such as within the hollow storage cavity 52. The electrical motor is preferably connected to the first member 12 such that when the user depresses a switch, the first member is rotated with respect to the second member 14, thereby compressing the resilient earplug.

In yet another alternative embodiment, a resilient earplug dispenser incorporates a resilient earplug shaper for automatically dispensing multiple compressed earplugs. When a user desires a pair of resilient earplugs, a switch is depressed causing a pair of resilient earplugs to enter a resilient earplug shaper. The resilient earplugs are then compressed within the resilient earplug shaper by rolling the earplugs between an outer and inner surface according to the embodiments of this invention, and the compressed resilient earplugs are then ejected from the apparatus for insertion into the ear of the user.

The foregoing description details certain preferred embodiments of the present invention and describes the best mode contemplated. It will be appreciated, however, that changes may be made in the details of the construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. An apparatus for compressing a resilient earplug having an initial outer diameter, said apparatus comprising:

a first member configured to rotate about a rotational axis, the first member having an outer surface for contacting the earplug, said outer surface being disposed around the rotational axis at a radial distance $R_1$ from and parallel to the rotational axis, where the radial distance $R_1$ continuously varies from a minimum value at a first location on the outer surface to a maximum value at a second location on the outer surface; and a second member having an inner surface for contacting the earplug, said inner surface disposed around the rotational axis at a substantially constant radial distance $R_2$ from and parallel to the rotational axis, where the radial distance $R_2$ is greater than the radial distance $R_1$, such that there is a space defined by $R_2-R_1$ for accommodating the earplug between the outer surface of the first member and the inner surface of the second member, wherein $R_2-R_1$ at the first location is greater than the initial outer diameter of the earplug, and $R_2-R_1$ at the second location is less than the initial outer diameter of the earplug, and wherein the earplug that is initially disposed at the first location within the space between the outer surface of the first member and the inner surface of second member is rolled and compressed between the two surfaces as the first member rotates about the rotational axis in relation to the second member, or as the second member rotates about the rotational axis in relation to the first member, and upon completion of rotation of the first or the second member with respect to the other, the earplug is disposed at the second location within the space between the outer surface of the first member and the inner surface of second member, resulting in a final outer diameter of the earplug that is less than the initial outer diameter.

2. The apparatus for compressing a resilient earplug of claim 1, wherein the outer surface of said first member defines a spiral, and the inner surface of said second member defines a circle.

3. The apparatus for compressing a resilient earplug of claim 1 wherein at least one of the outer surface of said first member and the inner surface of said second member is textured.

4. The apparatus for compressing a resilient earplug of claim 1, further comprising a cap member connected to said first member such that the cap member and the first member are configured to rotate together in relation to the second member, the cap member substantially covering the space between the outer surface of the first member and the inner surface of the second member.

5. The apparatus for compressing a resilient earplug of claim 4 wherein said cap member includes a first passageway in communication with the space between the outer surface of the first member and the inner surface of the second member, the first passageway having a size greater than the initial diameter of the earplug when the earplug is in an uncompressed condition.

6. The apparatus for compressing a resilient earplug of claim 4 wherein said cap member includes a second passageway in communication with the space between the outer surface of the first member and the inner surface of the second member, the second passageway having a size greater than the final diameter of the earplug when the earplug is in a compressed condition.

7. The apparatus for compressing a resilient earplug of claim 1, further comprising:
 a hollow storage cavity disposed within the first member, the hollow storage cavity having a closed end and an open end; and
 a removable cover member operable to engage and cover the open end of the hollow storage cavity.

8. The apparatus for compressing a resilient earplug of claim 7 wherein the hollow storage cavity is cylindrical and has a central axis substantially coinciding with the rotational axis and has an outer radius $R_3$ that is less than the radial distance $R_1$.

9. The apparatus for compressing a resilient earplug of claim 1 further comprising a bottom member connected to said second member such that the bottom member and the second member are configured to rotate together in relation to the first member, the bottom member substantially enclosing the space between the outer surface of the first member and the inner surface of the second member.

10. The apparatus for compressing a resilient earplug of claim 1, further comprising a ratchet mechanism comprising:
 a ratchet arm attached to the first member, said ratchet arm including one or more teeth members disposed at a distance $R_3$ from the rotational axis;
 a plurality of notches formed in the second member at the distance $R_3$ from the rotational axis,
 wherein the teeth members of the ratchet arm engage the notches of the second member thereby allowing only one direction of rotation of the first member with respect to the second member's.

11. An apparatus for compressing a resilient earplug having an initial outer diameter, said apparatus comprising:
 a first member configured to rotate about a rotational axis, the first member having an outer surface for contacting the earplug, said outer surface being disposed around the rotational axis at a constant radial distance $R_1$ from and parallel to the rotational axis; and
 a second member having an inner surface for contacting the earplug, said inner surface disposed around the rotational axis at a radial distance $R_2$ from and parallel to the rotational axis, where the radial distance $R_2$ is greater than the radial distance $R_1$, such that there is a space defined by $R_2-R_1$ for accommodating the earplug between the outer surface of the first member and the inner surface of the second member, and where the radial distance $R_2$ continuously varies from a maximum value at a first location on the inner surface to a minimum value at a second location on the inner surface,
 wherein $R_2-R_1$ at the first location is greater than the initial outer diameter of the earplug, and $R_2-R_1$ at the second location is less than the initial outer diameter of the earplug, and
 wherein the earplug that is initially disposed at the first location within the space between the outer surface of the first member and the inner surface of second member is rolled and compressed between the two surfaces as the first member rotates about the rotational axis in relation to the second member, or as the second member rotates about the rotational axis in relation to the first member, and upon completion of rotation of the first or the second member with respect to the other, the earplug is disposed at the second location within the space between the outer surface of the first member and the inner surface of second member, resulting in a final outer diameter of the earplug that is less than the initial outer diameter.

12. The apparatus for compressing a resilient earplug of claim 11, further comprising a ratchet mechanism comprising:
 a ratchet arm attached to the first member, said ratchet arm including one or more teeth members disposed at a distance $R_3$ from the rotational axis;
 a plurality of notches formed in the second member at the distance $R_3$ from the rotational axis,
 wherein the teeth members of the ratchet arm engage the notches of the second member thereby allowing only one direction of rotation of the first member with respect to the second member.

13. An apparatus for compressing a resilient earplug having an initial outer diameter, said apparatus comprising:
 a first member configured to rotate about a rotational axis, the first member having an outer surface for contacting the earplug, said outer surface being disposed around the rotational axis at a radial distance $R_1$ from and parallel to the rotational axis, where the radial distance R1 continuously varies from a minimum value at a first location on the outer surface to a maximum value at a second location on the outer surface; and
 a second member having a substantially planar inner surface for contacting the earplug, said inner surface disposed about the rotational axis at a radial distance $R_2$ from the rotational axis, where the radial distance $R_2$ is greater than the radial distance $R_1$, where the radial distance $R_2$ continuously varies from a maximum value at a first location on the inner surface to a minimum value at a second location on the inner surface, such that there is a space defined by $R_2-R_1$ for accommodating the earplug between the outer surface of the first member and the inner surface of the second member, wherein $R_2-R_1$ at the first location is greater than the initial outer diameter of the earplug, and $R_2-R_1$ at the second location is less than the initial outer diameter of the earplug, and wherein the earplug that is initially disposed at the first location within the space between the outer surface of the first member and the inner surface of second member is rolled and compressed between the two surfaces as the first member rotates about the rotational axis in relation to the second member, or as the second member rotates about the rotational axis in relation to the first member, and upon completion of rotation of the first or the second member with respect to the other, the earplug is disposed at the second location within the space between the outer surface of the first member and the inner surface of second member, resulting in a final outer diameter of the earplug that is less than the initial outer diameter.

\* \* \* \* \*